United States Patent
Borghese et al.

(10) Patent No.: US 7,835,489 B2
(45) Date of Patent: Nov. 16, 2010

(54) METHOD AND APPARATUS FOR SIMPLIFIED PATIENT POSITIONING IN DENTAL TOMOGRAPHIC X-RAY IMAGING

(75) Inventors: Nunzio Alberto Borghese, Milan (IT); Iuri Frosio, Sorisole (IT); Eros Nanni, Castel S. Pietro (IT); Gerardo Rinaldi, Milan (IT); Giuseppe Rotondo, Pantigliate-Milan (IT)

(73) Assignee: Cefla S.C. (IT)

( * ) Notice: Subject to any disclaimer, the term of this patent is extended or adjusted under 35 U.S.C. 154(b) by 0 days.

(21) Appl. No.: 12/468,541

(22) Filed: May 19, 2009

(65) Prior Publication Data

US 2009/0323891 A1   Dec. 31, 2009

(30) Foreign Application Priority Data

May 19, 2008   (EP) .................................. 08156495

(51) Int. Cl.
*A61B 6/00*   (2006.01)
*A61B 6/14*   (2006.01)
(52) U.S. Cl. .......................................... 378/20; 378/38
(58) Field of Classification Search .................. 378/20, 378/38, 68, 177, 195, 208
See application file for complete search history.

(56) References Cited

U.S. PATENT DOCUMENTS

| | | | |
|---|---|---|---|
| 4,589,122 A | | 5/1986 | Nieminen |
| 5,224,140 A | | 6/1993 | Virta et al. |
| 5,425,065 A | | 6/1995 | Järvenin |
| 5,431,162 A | | 7/1995 | McArdle |
| 5,784,429 A | * | 7/1998 | Arai ............................ 378/38 |
| 5,921,927 A | | 7/1999 | McArdle |
| 6,018,563 A | * | 1/2000 | Arai et al. ..................... 378/39 |
| 6,118,842 A | * | 9/2000 | Arai et al. ..................... 378/39 |
| 6,233,305 B1 | | 5/2001 | Müller |
| 6,424,694 B1 | | 7/2002 | Molteni et al. |
| 7,336,763 B2 | * | 2/2008 | Spartiotis et al. .............. 378/40 |
| 7,577,232 B2 | * | 8/2009 | Tachibana et al. ............. 378/39 |
| 2002/0122537 A1 | | 9/2002 | Yoshimura |
| 2004/0247069 A1 | | 12/2004 | Arai et al. |
| 2005/0117696 A1 | | 6/2005 | Suzuki et al. |
| 2008/0063139 A1 | | 3/2008 | Pantsar et al. |

FOREIGN PATENT DOCUMENTS

DE   3937077 A1   5/1990

(Continued)

OTHER PUBLICATIONS

"Digital x-ray tomosynthesis: current state of the art and clinical potential"; James T Dobbins III and Devon J Godfrey; Sep. 16, 2003; 42 pages (Continued)

*Primary Examiner*—Irakli Kiknadze
(74) *Attorney, Agent, or Firm*—St. Onge Steward Johnston & Reens LLC

(57) ABSTRACT

An apparatus and a method is proposed which allow for a simplified patient positioning based on the selection of a region of interest for the tomographic image of the dentition of a patient. The region of interest is selected on a previously acquired panoramic image of the dentition of the patient.

20 Claims, 2 Drawing Sheets

FOREIGN PATENT DOCUMENTS

| | | |
|---|---|---|
| DE | 19941668 A1 | 3/2000 |
| DE | 10338145 A1 | 3/2005 |
| DE | 112006002694 T5 | 9/2008 |
| EP | 1961383 A1 | 8/2008 |
| JP | 2006314774 A | 11/2006 |
| WO | 2004014232 A1 | 2/2004 |
| WO | 2004039261 A1 | 5/2004 |
| WO | 2007046372 A1 | 4/2007 |

OTHER PUBLICATIONS

"Effect of head positioning in panoramic radiography in vitro study"; Q. Xie et al; Dentomaxillofac. Radiol., vol. 25, No. 2, pgs (1996); pp. 61-66.

European Search Report; EP 08 15 6495; Dec. 2, 2008; 4 pages.

"History of Panoramic Radiography"; Hallikainen, D.; Acta Radiologica; vol. 37(3) Part II; May 1996; pp. 441-445.

Lehmann, T. et al. "IDEFIX—Identification of dental fixtures in intraoral X-rays", Proc. SPIE 2710, p. 584-595 (1996).

"Maximum Likelihood Transmission Image Reconstruction for Overlapping Transmission Beams"; Jeffrey A. Fessler, Daniel F. Yu, and Edward P. Ficaro; (2000) 5 pages.

Sahiwal, I. G. et al., "Radiographic identification of nonthreated endoseous dental implants", J. Prosthet. Dent. 87, 552-562 (2002).

"Statistical inversion for medical x-ray tomography with few radiographs: I. General theory" S. Siltanen, V. Kolehmainen, S. Järvenpää, J. P. Kaipio, P. Koistinen, M. Lassas, J. Pirttilä and E. Somersalo; Phys. Med. Biol. 48 (2003) pp. 1437-1463.

Braun, S. et al.; "The shape of the human dental arch"; The Angle Orthodontist; vol. 68, No. 1, p. 29-36, 1998.

Mundrak, Jörg: VT-All the Essential Information for Implantology, Dental Products Reports Europe (dprEurope), Sep. 2008, 3 pages.

InstrumentariumL Orthopantograph, Orthceph, OP200 - Digital and Film, 2007; 28 pages.

Instrumentarium: Orthopantograph OP200D, Orthoceph OC200D, User Manual, Document Code D500319 rev 3, Feb. 1, 2008; 150 pages.

\* cited by examiner

METHOD AND APPARATUS FOR SIMPLIFIED PATIENT POSITIONING IN DENTAL TOMOGRAPHIC X-RAY IMAGING

CROSS-REFERENCE TO RELATED APPLICATIONS

This application claims priority of European Application No. 08 156 495 filed on May 19, 2008. The disclosure of this application is hereby incorporated by reference in its entirety, as part of the present disclosure.

FIELD OF THE INVENTION

A method for dental tomographic X-ray imaging, the method comprising the steps of:
  positioning a patient in an X-ray apparatus by a head support that has been used for the acquisition of a panoramic image and that keeps the patient in the same position as for the acquisition of the panoramic image;
  selecting a region of interest for a local tomographic imaging process based on the panoramic image of the dental arch of the patient at any point of the dental arch;
  calculating the parameters for a trajectory applicable for the local tomographic imaging process by the control unit based on the selection of the region of interest; and
  performing an imaging process by the X-ray apparatus under the control of a control unit by moving the imaging system along the trajectory.

The invention further relates to an apparatus for implementing the method.

BACKGROUND OF THE INVENTION

Such a method and such an apparatus are known from US 2005/0117696 A1. According to the known method a panoramic image is taken from the dentition of a patient. The panoramic image is further used for selecting a region of interest. Subsequently, a tomographic imaging process is performed for obtaining a three-dimensional image of the region of interest. For both processes the patient is kept stationary at the same place using a single head support.

One disadvantage of the known method and the known apparatus is that the apparatus is primarily arranged for computer tomography based on two-dimensional projection images taken by digital flat panel detectors. The flat panel detectors can be detectors with scintillators that transform the incident X-ray radiation into light in the optical wavelength range. The light generated by the scintillators is then detected by optical detectors. As set forth in detail in US 2008/0063139 A1, this type of detectors can hardly be used for panoramic imaging since these detectors are not fast enough for continuous exposure. US 2008/0063139 A1 therefore proposes to use CMOS detectors based on CdTe for panoramic imaging. However, these detectors are quite expensive. In addition, these detectors must be read out at a high frame rate, so that the read-out electronic must be relatively fast. Furthermore large storage volumes are required for storing the vast amount of data.

U.S. Pat. No. 5,921,927 A discloses a further method and apparatus. In a first step of the known method an imprint of the mouth of the patient is taken. Afterwards, the imprint is attached to the radiographic apparatus through a specific holder. The imprint and the holder form together a bite unit. The holder is then moved manually by the clinical operator, to bring it in the desired position. According to the known method, an optical adjustment device is used to align the bite unit of the apparatus such that a local tomographic image can be taken from a particular region of dentition of the patient. The optical adjustment device is provided with a laser whose beam can be used to mark the region of tomographic imaging on the imprint in the bite unit. For adjusting the patient, the operator moves the bite unit until the point of interest on the imprint matches with the mark of the laser beam on the imprint.

U.S. Pat. No. 6,424,694 B1 discloses a bite support that is translated and oriented by an external off-line alignment accessory device, so that the center of the volume of interest falls under the reference marking of a transparent plexiglas template. The device is then repositioned on the system to perform the tomographic examination.

In both cases, the operator has to modify position and orientation of the bite support manually in order to adapt it to the patient and to the desired volume of interest. This procedure is time consuming and it may introduce substantial errors in patient positioning.

Local tomographic analysis is a widely used examination in the field of dental surgery, in particular in the field of implantology. Conventional tomography, tomosynthesis, and local cone beam computerized tomography (=CB-CT) are well known techniques, which generate a volumetric reconstruction of the analyzed anatomical districts, delivering a low radiation dose in the patient tissues.

To achieve the maximum efficiency, patient positioning is critical. In particular the patient's position with respect to the radiographic apparatus has to be set such that the center of the volume of interest coincides with the center of the volume which will be reconstructed. This problem is common to conventional tomography, tomosynthesis and CB-CT.

Conventional tomography and tomosynthesis are limited angle of view tomographic methods that generate a set of parallel slices orthogonal to main direction of projection, where resolution is minimum along the direction orthogonal to the slices, and maximum along the slices. Therefore, conventional tomography and tomosynthesis also require that the patient is adequately oriented in the three-dimensional space, with respect to the radiographic apparatus. Incorrect orientation of the acquired volume may introduce blurring of the interesting anatomical structures, making structure identification difficult and measurements inaccurate.

For instance, volume orientation is critical when measurements have to be taken along a preferential direction. This is common to different dental applications like implantology, where the knowledge of the lower or upper jaw cross-section and of the nerve canal position is fundamental to plan an accurate, risk free, implant. In this situation, the slices acquired with conventional tomography or tomosynthesis should be orthogonal to the lower or upper jaw profile, to allow the maximum resolution of the anatomical structures and accurate measurements of the dimension of the anatomical structures of interest.

For CB-CT the orientation of the volume is also important, especially if the reconstructed volume has an anisotropic shape, or if a limited angle of view acquisition scheme is adopted.

U.S. Pat. No. 5,425,065 A discloses a method and an apparatus for taking panoramic images of the dentition of a patient. The panoramic radiography is based on the theory of orthopantomography, which has been established for a long time. The basic principle of orthopantomography is a coordinated movement of the X-ray source and detector pair, which allows focusing on the structures lying on a predefined surface, blurring out at the same time structures outside the focal plane. This approach is also used in panoramic radiography to focus on the patient dental arch, blurring all the other anatomical structures of the skull.

BRAUN, S. et al., The shape of the human dental arch, The Angle Orthodontist, Vol. 68, No. 1, p. 29-36, 1998 contains data on a template of the human dental arch.

SAHIWAL, I. G. et al., Radiographic identification of non-threaded encloseous dental implants, J. Prosthet. Dent. 87, 552-562 (2002) and LEHMANN, T. et al. IDEFIX—Identification of dental fixtures in intraoral X-rays, Proc. SPIE 2710, p. 584-595 (1996) disclose methods for the identification of fixtures within the dental arch such as dental implants.

SUMMARY OF THE INVENTION

Proceeding from this related art, the present invention seeks to provide a simplified method and an apparatus for dental tomographic X-ray imaging with improved image quality.

This object is achieved by a method having the features of the independent claim. Advantageous embodiments and refinements are specified in claims dependent thereon.

In the method and in the apparatus, one single head support is used for the acquisition of the panoramic images and for the tomographic imaging process. The head support keeps the patient for the tomographic imaging process in the same position as for the acquisition of the panoramic image. The region of interest is selected at any point of the dentition of the patient based on a panoramic image of the dental arch of the patient. Furthermore, the parameters for the trajectory applicable for the local tomographic imaging process are calculated by the control unit based on the selection of the region of interest. The localization of the region of interest is based on an actual panoramic image of the dentition of the patient. Since the spatial relation between the panoramic image and the actual position of the dentition of the patient is known an accurate spatial relation between the region of interest and the actual position of the dentition can be established after the region of interest has been selected by the operator. Since the actual position of the dentition is known, the operational parameters of the imaging system can further be chosen appropriately. By allowing rotations and translation during the tomographic imaging process, the spatial extension of the detector can be reduced and the available detector area can be used effectively. For instance, a linear shaped narrow beam detector can be used for performing scanning movements. For allowing appropriate trajectories with respect to regions of interest, whose positions can be chosen at any point of the dentition, the rotational axis can be shifted by more than +/−60 millimeter along a transversal plane. Although the apparatus and the method comprise the relatively simple basic structure of an apparatus and a method specifically designed for panoramic imaging, the use of the method and the apparatus results in a high image quality of the recorded tomographic images, wherein the tomographic images can be taken at any point of the dentition.

In one preferred embodiment, the panoramic image is acquired in real-time prior to the selecting step. Thus a particularly accurate relationship between the actual position of the dentition in three-dimensional space and the panoramic image can be established.

Preferably, a template dental arch is used instead of the actual dental arch for establishing a relation between the image points on the panoramic image and the three-dimensional space. In most cases using the template dental arch will be sufficient, since the actual dental arch can be accurately reproduced by the template dental arch.

The template dental arch can also be corrected for the lower or upper jaw taking into account the inclination of the dentition with respect to the vertical direction in order to improve the spatial relation between the actual dentition and the image points of the panoramic image.

The selection of the region of interest preferably includes a selection of the position and orientation of the region of interest in the three-dimensional space. Since the spatial resolution is not isotropic for tomographic imaging with a limited angle of view the orientation of the region of interest is important for the usability of the tomographic images.

In an embodiment of the method, a repositioning of the patient is performed prior to the step of moving the imaging system along the trajectory taking into account cinematic constraints of the system. In this case it will be possible to perform a tomographic imaging process even if the mechanical structure of the imaging system does not allow taking a tomographic image at any point of the dentition of the patient.

The repositioning is preferably made by a roto-translation of the head support system, based on displacement data calculated and provided by the control unit.

The repositioning can also be automatically made by the head support system upon user command, performing the roto-translation of the head support system by controlling particular actuators of the head support system. Thus, the operator can give the patient a warning before the head of the patient is repositioned.

The extent of the repositioning is preferably calculated by the system based on optimization criteria such as dose minimization, maximum angle of view, minimum time of acquisition, maximum distance between patient and moving components of the radiographic apparatus resulting in a low dose for the patient in combination with high quality of the tomographic images.

The quality of the tomographic images can be further increased if a local analysis of the panoramic image is performed for identifying fixtures or other metallic objects, and if the operational parameters including X-ray dose and angle of view are varied in dependency of the output of the local analysis.

The dose to which the patient is exposed can particularly be reduced if, based on the vertical position and extension of the selected region of interest, at least one vertical X-ray collimator is automatically or manually operated avoiding unnecessary exposure of the patient tissues lying outside of the region of interest.

If the radiographic apparatus is equipped with a limited number of acquisition trajectories for the tomographic imaging process a movable positioning device is used to get the proper position and orientation of the patient. In some cases also a roto-translational motion of the patient is needed to bring the region of interest to the correct position and orientation if the radiographic apparatus is equipped with a limited set of trajectories that do not allow performing the tomographic reconstruction of any point of the dental arch.

However, if the radiographic apparatus is capable of acquiring a set of radiographic images for the tomographic examination in any point of the dentition a fixed positioning device might be used.

For increasing the quality of the reconstructed volume, the data of the panoramic radiography can be used as an additional projection image from a different point of view added to the data set of the projection images, thus improving the quality of the tomographic reconstruction. The reconstructed volume and the panoramic image can also be displayed together in a three-dimensional representation.

BRIEF DESCRIPTION OF THE DRAWINGS

Further advantages and properties of the present invention are disclosed in the following description, in which exemplary embodiments of the present invention are explained in detail on the basis of the drawings.

DETAILED DESCRIPTION OF THE INVENTION

Figure 1:
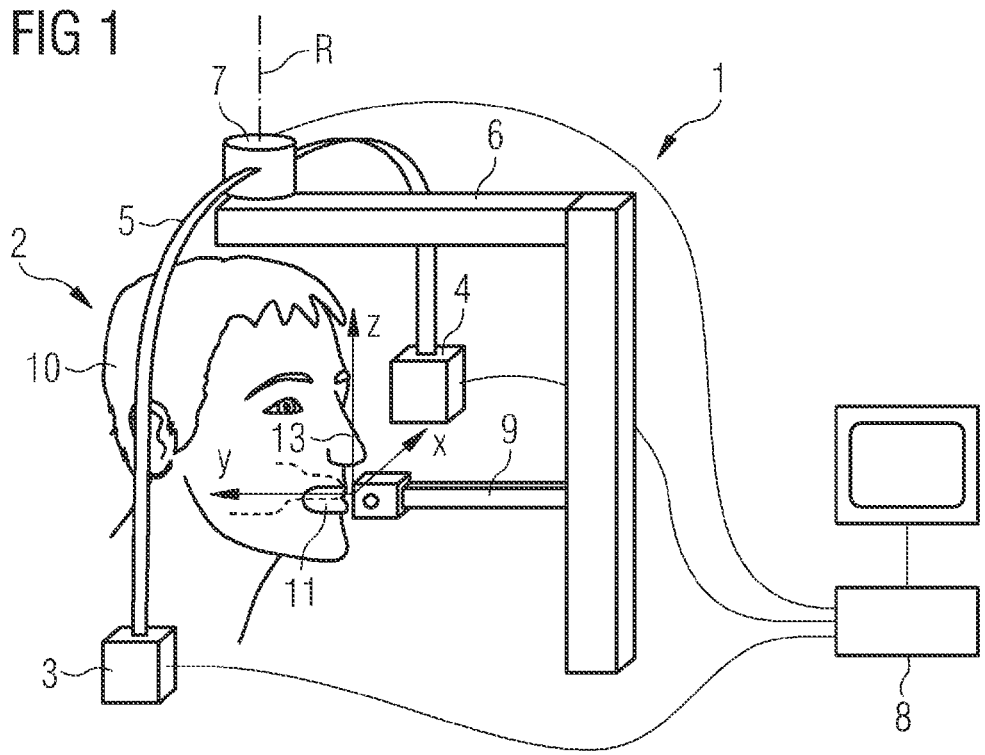
FIG. 1 shows a patient who bites the bite unit of a radiographic apparatus to get the correct positioning.

FIG. 1 shows an apparatus 1 used for taking tomographic X-ray images from the dentition of a patient 2. According to FIG. 1 the apparatus 1 comprises an X-ray imaging system including an X-ray tube 3 and an X-ray detector 4, held by a pivotable support 5. The detector 4 may be a digital detector provided with a scintillator that converts the incident radiation into light that is detected by an optical detector such as a CCD-sensor. Advantageously, the detector 4 is a digital detector that converts the incident X-ray radiation directly into electrical signal without scintillator, such as a CMOS detector based on CdTe. The x-ray detector 4 can in particular be a vertical aligned linear shaped digital detector comprising a few ten vertically aligned rows of detector pixels. For instance, the detector 4 may comprise 60 vertically aligned rows of 1400 detector pixels, wherein each detector pixel covers an area of 100×100 μm. In consequence, the number of pixels in a particular row is generally greater than the number of rows. The pivotable support 5 is mounted on a stand 6 via a drive unit 7 and can be pivoted around a rotational axis R. The rotational axis R can be moved along a transversal plane extended by the X-axis and the Y-axis.

The source 3, the detector 4 and the drive unit 7 are connected to a control unit 8, which controls the movement and the operation of the tube 3 and the detector 4 during the imaging process. In the following the assembly formed by the tube 3 and the detector 4 is also called imaging system.

The control unit 8 is provided with a display for displaying images taken by the apparatus 1 and may also be provided with various input devices such as a keyboard or a mouse for inputting data or commands to the apparatus 1.

The apparatus 1 further comprises a head support 9 for positioning a head 10 of the patient 2 in a predefined position with respect to the apparatus 1. The head support 9 can be formed by a bite unit 11 and may also comprise a headrest that is in contact with the head 10 at a variety of separate locations beyond the teeth of the patient 2. The headrest may, for instance, comprise at least two struts that contact the head 10 separately at two places and ensure a stable and accurate positioning of the head 10. During the imaging process, the patient 2 bites on the bite unit 11 of the apparatus 1 to get the correct positioning of a dental arch 12 of the patient 2.

The apparatus may also be equipped with a laser guiding system for positioning the patient 2. Such a laser guiding system may provide optical marks on the head 10 of the patient 2 for aligning the patient 2 with the apparatus 1, in particular for aligning the patient 2 with the X-ray imaging system.

In FIG. 1, an absolute reference system 13 with a vertically aligned Z-axis is shown to be located in the center of the bite unit 11 in the region of the incisors. The Y-axis extends towards the spine of the patient 2 whereas the X-axis extends in a lateral direction.

Figure 2:
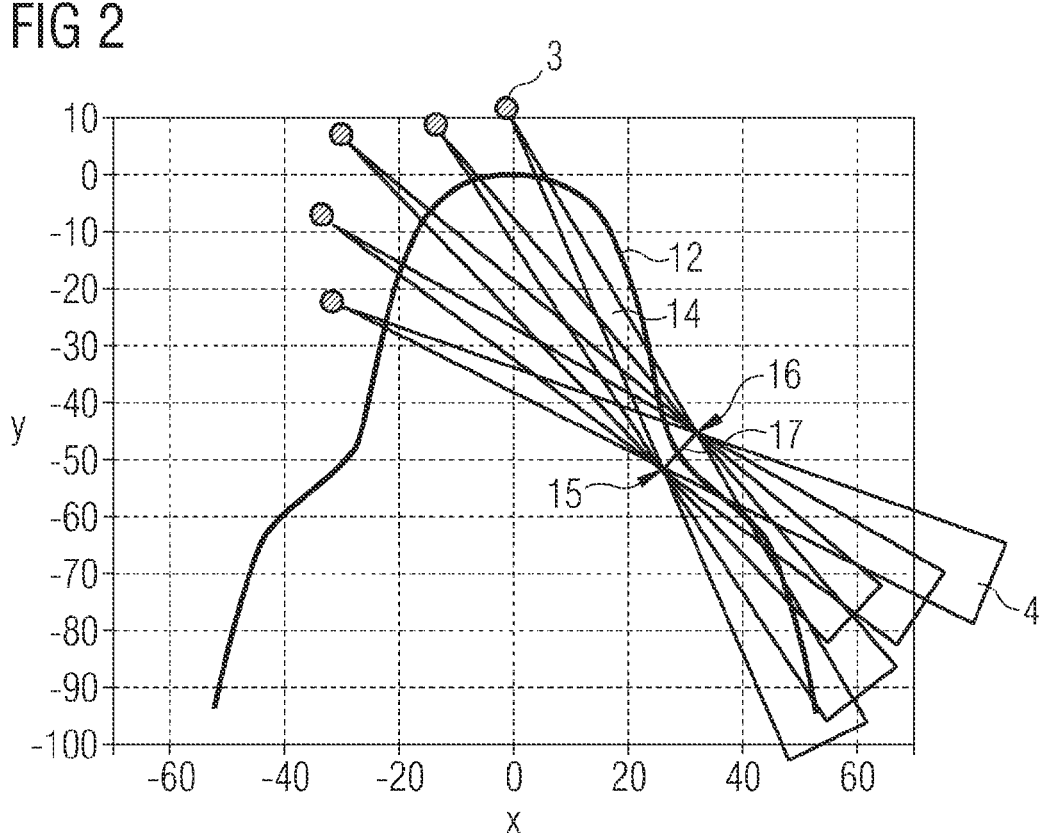
FIG. 2 shows a dental arch of a patient together with five projections.

FIG. 2 shows a typical acquisition scheme, in which the tube 3 and detector 4 approximately rotate around the interesting anatomical structure. According to FIG. 2 the dental arch 12 extends in the XY-plane of the reference system 13. The dental arch 12 is shown as a continuous thick curve. A set of five projection images 14 is also shown. The origin of the five projection images 14 lies in the tube 3, which follows a preset trajectory for taking a tomographic image of a region of interest of the dental arch 12. The motion of the tube 3 is coupled to a corresponding motion of the detector 4 on the opposite side of the head 10. Radiographic images of the head 10 of the patient 2 are generated on the detector 4 by the projection images 14. From the projection images 14, a three-dimensional image of a target volume 15 can be reconstructed by the control unit 8 using a tomographic reconstruction method such as algebraic methods, frequency based methods or tomosynthesis. The target volume 15 generally corresponds to a region of interest 16 selected by the operator. The resolution within the target volume 15 is best in a focal plane 17, which corresponds to a common intersection plane of the projections. In a direction orthogonal to the focal plane 17 along the main direction of projection the resolution is lowest.

The apparatus 1, in particular the control unit 8, is also provided with means for selecting the region of interest 16 for a local tomography or tomosynthesis. It should be noticed that, given a certain trajectory of the tube 3 and the detector 4, the local target volume 15 which can be reconstructed is uniquely determined. Furthermore, the dental radiographic apparatus, such as the apparatus 1, have strong kinematics constraints that do not allow performing tomographic reconstruction at any desired target volume 15 along the dental arch 12. Thus, a limited number of trajectories are typically available, allowing tomographic reconstruction only on a subset of predefined oriented target volumes in the three-dimensional space. The patient 2 has therefore to be moved in order to position and orient the head 10 such that the desired local region of interest 16 falls inside one of these predefined target volumes 15.

Figure 3:
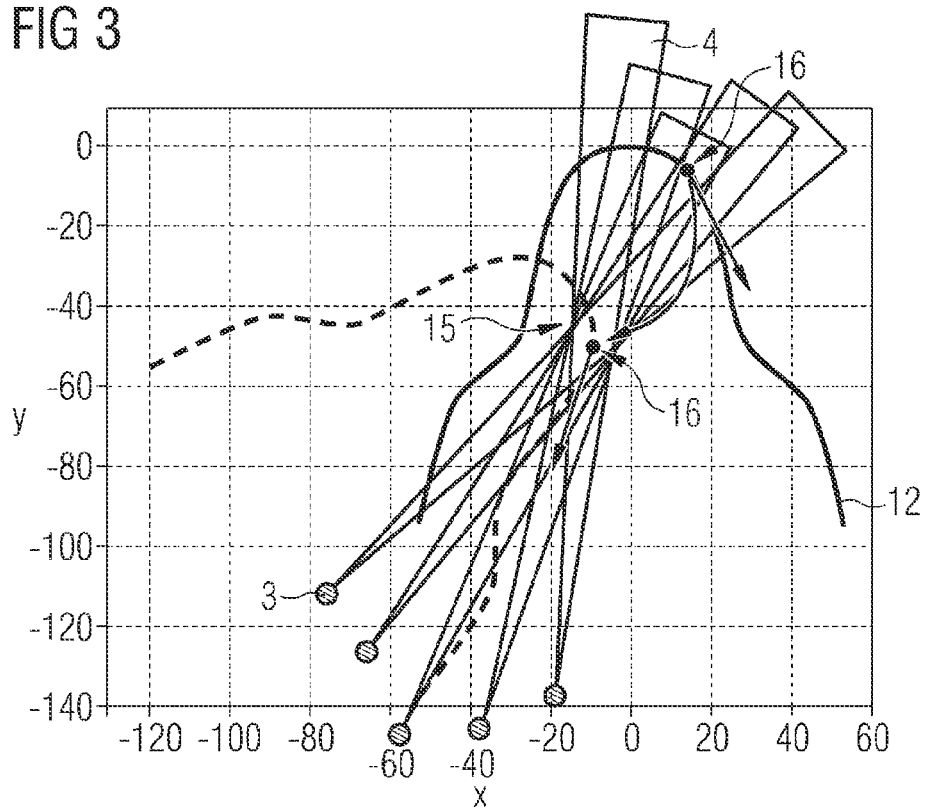
FIG. 3 shows the dental arch of FIG. 2 displaced at another position.

In FIG. 3 the dental arch 12 from FIG. 2 has been moved, since a different position and orientation are required to bring the anatomical structures of the region of interest 16 within an allowable target volume 15. In FIG. 3, the reference position is depicted by a solid line and the patient 2 has been moved to the position by a dashed line by moving the bite unit 11 in the correct orientation and position. The arrows indicate the tangential directions to the dental arch 12.

Positioning is generally a time consuming and complex process, requiring iterative steps of positioning of the patient 2, alignment of dedicated accessories and verifications by the operator with substantial risk of positioning errors.

Figure 4:
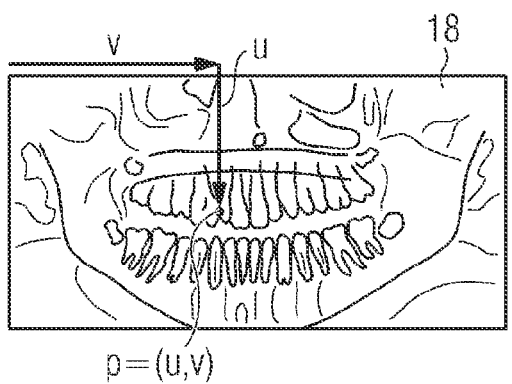
FIG. 4 depicts a typical panoramic radiography in panel, on which a local tomographic reconstruction of the root of the second upper molar is set up.

In the method described herein, a panoramic radiography 18 as shown in FIG. 4 is used for positioning the target volume 15 with respect to the imaging system. To obtain a panoramic radiography 18 of high quality, the patient 2 shall always be accurately positioned with respect to the system, as shown in FIG. 3, so that during the image acquisition the imaging system focuses exactly on the dental arch 12. For these purposes, the following procedure is adopted: The patient 2 bites the bite unit 11, which is rigidly connected to the radiographic apparatus 1. In addition, the patient 2 may get in contact with the head rest and may be positioned using the laser guiding system. As a consequence, the central point of the dental arch 12 lies in a known position. Then, a clinical operator adjusts the orientation of the patient 2 such that the dental arch 12 is horizontal and no tilt in the dental arch is present. Once the positioning procedure is terminated, the dental arch 12 in the XY-plane is well superimposed to a template dental arch 19 as will be outlined in detail in connection with FIGS. 4 and 5.

For establishing a spatial relation between the target volume 15 and the radiographic image, the shape of the dental arch 12 has advantageously to be known a priori, such that the coordinated movement of the X-ray tube 3 and the detector 4 focuses on the region of interest 16 of the dental arch 12. The mean shape of the jaw in the XY-plane has been accurately estimated by many authors: it is well approximated by a piecewise polynomial function which can be adapted to the size of the patient 2. In the following, we will refer to it as the template dental arch 19. The template dental arch 19 is also used for controlling the motion of the imaging system while taking the panoramic radiography 18 depicted in FIG. 4. On this panoramic radiography 18 a local tomographic reconstruction of the root of the second upper molar is set-up. The pixel p(u,v) in the center of the interesting area is identified by its row index u and column index v of the panoramic radiography 18.

Figure 5:
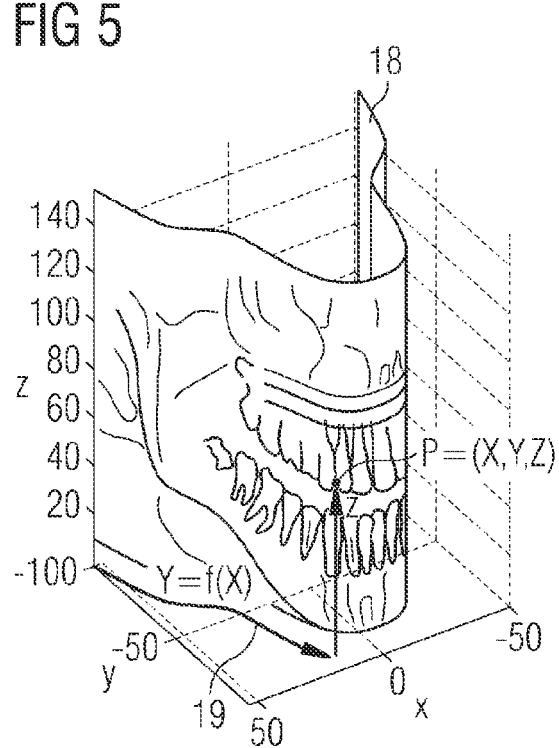
FIG. 5 shows a three-dimensional representation of the panoramic radiography form FIG. 4 mapped on a template arch.

The same panoramic radiography 18 mapped onto a template dental arch 19 is shown in FIG. 5. As can be seen from FIG. 5, the surface of the panoramic radiography follows the curve Y=f(X) and it is parallel to the vertical Z-axis. For controlling the motion of the imaging system the coordinates of the point p(u,v) in the reference system 13 have to be known. The three-dimensional coordinates of the point P=(X, Y, Z), corresponding to p(u,v) in the panoramic radiography 18, can then be computed as follows:

It is assumed that the panoramic radiography 18 of the patient 2 has been previously acquired as depicted in FIG. 4. Each pixel p=(u, v) of the panoramic radiography 18 can be associated to a single three-dimensional point, P=(X, Y, Z), lying on a vertical surface passing through the template dental arch, [X, f(X), Z]. Therefore a biunivocal correspondence can be written between the points on the panoramic radiography 18 and the points of the panoramic radiography 18 positioned in three-dimensional space following the template dental arch 19. For arranging such biunivocal correspondence with the template dental arch 19, information associated with the panoramic radiography 18 and relating to the type of panoramic radiography 18 and the geometry of the acquisition of the radiography 18 can be used.

The coordinates X, Y, Z can be computed from u, v as follows:

The vertical position, that is the Z coordinate, is computed by considering that the surface focused in the panoramic radiography 18 is perpendicular to the horizontal XY-plane; therefore the height of point P above the horizontal XY-plane is linearly proportional to the row index u of the panoramic radiography 18 as:

$$Z = k\,u + Z_0 \quad (1)$$

where k depends on the vertical pixel size and $Z_0$ is the height of the first line of the panoramic image.

The position of P on the horizontal plane, [X, Y], is associated with the column index v on the panoramic radiography 18. Such relationship can be computed from the trajectory used to acquire the panoramic radiography 18; the focused surface corresponds to the template dental arch 19, therefore:

$$X = X(v) + X_0 \quad (2a)$$

$$Y = Y(v) + Y_0 \quad (2b)$$

This correspondence can be stored in a look-up table as the number of column indexes is finite. All the constants and parameters can be derived from factory specifications.

We explicitly note that the tangential direction to the template dental arch 19, in the following the versor f'(X), can be computed for each point of f(X). This versor indicates the local orientation of the mandible. Given the position XY onto the template dental arch 19, the tangential direction to the template dental arch 19 is easily derived, for instance analytically, using the expression of f(X) for the template arch, or numerically, given a set of points belonging to the template arch. These data can also be pre-computed and stored.

Therefore, we can assume that the orientation and the position of the volume of interest 16 are completely determined with respect to the position used when the panoramic radiography 18 of the patient 2 was acquired (reference position).

For implementing the method described herein the apparatus 1 is provided with extended kinematic capability, which avoids in most cases the need to correct the alignment of the head 10 when local tomography is performed.

In a first preferred embodiment, no motion of the head support 9 and correction of alignment of the head 10 of the patient 2 are required for any tomographic examination. Only appropriate movements, in particular translations and rotations of the components of the imaging system are involved, thus leading to a simplified solution for the positioning problem. In particular, the drive unit 7 and the stand 6 are arranged such that the rotational axis R can perform an extended movement along a transversal plane extended by the X-axis and the Y-axis. The rotational axis R can be shifted by more than +/−50 millimeter, preferably by more than +/−60 millimeter or even by more than +/−70 millimeter with respect to a neutral position of the rotational axis. These translations and rotations of the imaging system can be performed during the positioning of the imaging system with respect to the patient 2 and during the acquisition of the projection images 14 for the tomographic reconstruction. In particular, if the detector 4 is a vertically aligned linearly shaped detector, the detector can perform a lateral scanning movement in a horizontal direction allowing the acquisition of two-dimensional projection images 14. It should be noted that the angular range of the rotation of the imaging system may extend over 3600, over 180° or may be limited to an angular range less than 180° depending on the requirements of the tomographic reconstruction method. However, the shape of the trajectories used during the acquisition of the projection images 14 generally depart from the circular form.

It should be emphasized that, in this embodiment, the patient 2 is kept fixed in the same positioning as for the panoramic radiography 18 and that there is no need of a movable head support system dedicated for tomographic examinations.

After the acquisition of the panoramic radiography 18, the clinical operator selects the pixel of interest p in the panoramic radiography, and eventually the required angle of view, which is typically transversal or longitudinal: The corresponding point P and versor TP, describing the center and the orientation of the volume of interest 16, are then automatically computed.

Then the operator starts the execution of the tomographic trajectory, the patient 2 is held by the same head support 9, which has been used during the acquisition of the panoramic radiography 18, so avoiding unnecessary repositioning. During the trajectory, the tube 3 and the detector 4 is driven such that a set of projections, aimed to the reconstruction of a target volume 15 centered in P and oriented along TP, is executed. It should be noted that a variety of different tomographic trajectories can be used for the tomographic imaging. The tomographic trajectories can also be adapted individually to the actual position and orientation of the region of interest 16. For these purposes, the control unit 8 is arranged for calculating the parameters of the trajectory individually depending on parameters of the region of interest such as the width of the region of interest 16 along the dental arch, the depth of the region of interest 16 in a lateral transversal direction of the dental arch, the height of the region of the interest 16 and the volume and orientation of the region of interest 16. The control unit may further also calculate the parameters of the trajectory depending on parameters associated with the geometry of the acquisition of the panoramic image. The height of the region of interest 16 may also be taken into account by choosing an appropriate collimator for the X-ray radiation.

In a second alternative embodiment, a motion of the head support 9 and a correction of the alignment of the head 10 are required only for limited volume positions corresponding to specific kinematic constraints of the tomographic apparatus 1. In such cases adjustment movements of the head support 9 can be automatically accomplished by the system, based on the numeric data output available by the method.

This alternative embodiment is required when, for at least one position of the volume of interest, the kinematic constraints of the imaging system do not allow execution of the tomographic trajectory without movement of the head support 9 and of the patient 2.

Therefore, after the acquisition of the panoramic radiography 18, the clinical operator selects the pixel of interest p in the panoramic radiography 18, and eventually the required angle of view, typically transversal or longitudinal: The corresponding point P and versor TP, describing the center and the orientation of the region of interest 16, are then automatically computed.

If the selected volume lies in a forbidden territory, where the trajectory cannot be executed due to the kinematic constraints of the system, the need arises to move the patient 2 and hence the region of interest 16 in a permitted region, where the trajectory can be executed.

The radiographic apparatus 1 according to the second embodiment can coordinately move the tube 3 and the detector 4, such that a trajectory related to the volume centered in $C_0$ with orientation $T_0$ can be executed.

The patient 2 has to be roto-translated with respect to the position and orientation assumed during the acquisition of the panoramic radiography 18, such that the forbidden region of interest 16 at position C' with orientation T' reaches the permitted position $C_0$ with orientation $T_0$ by a roto-translation.

This roto-translation has to be performed using the degrees of freedom allowed by the head support system. The parameters which define it, $Q_0=Q(C', C_0, T', T_0)$, can be derived taking into account the condition $C'=C_0$ and $T'=T_0$ at the end of the motion.

The movable head support system of the radiographic apparatus 1 is then automatically relocated according to the parameters $Q_0$. Lastly, the patient 2 is repositioned by the head support system and the acquisition can start.

Typically, orthopantomographs provide tomographic trajectories that allow volume reconstruction in predefined positions $C_n$ and orientation $T_n$ in the three-dimensional space, where n=1 ... N and N is the number of possible trajectories.

Therefore, before implementing the roto-translation described by $Q_n$, the system may decide or ask the user for a choice of the most adequate trajectory based on optimization criteria such as for instance the comfort of the patient 2 or the minimization of the path.

The method described so far advantageously apply to tomographic machines which comprise a limited range of acquisition angles. However, if a CB-CT machine with a 180° or 360° acquisition angle is considered, the volume orientation is less important, since the resolution of the reconstructed volume is generally isotropic. In this case, the proposed method could still be used to automatically position the patient with respect to the radiographic apparatus with high accuracy, discarding his orientation.

The knowledge on the orientation of the patient 2 can also be used to optimize the acquired radiographic images with respect to the reconstruction algorithm or to the dose released into the patient tissue. For instance, for a CB-CT machine acquiring data with a 180° acquisition angle, the patient can be oriented such that the dose released to some important tissues, such as the brain or the spine, is limited.

The methods described herein can also be modified with respect to the usage of the panoramic and tomographic data:

As previously stated, the reconstruction of a local volume from a set of projections taken from a limited angle of view suffers of a limited resolution along the main direction of projection. The local data provided by the panoramic radiography 18 can be integrated with the reconstructed volume to increase the resolution.

This integration can be done numerically; in this case, a specific algorithm has to be adopted. For instance, the panoramic radiography 18 can be included in the set of projections adopted for the tomographic reconstruction of the volume.

A more simple integration of the data can be performed by simultaneous visualization of the reconstructed volume and the panoramic radiography 18 in the three-dimensional space. This solution requires only the adoption of a three-dimensional graphic interface.

The method can also be used to design particular acquisition trajectories, for instance, aimed at the optimization of the projections if metallic objects (fixtures) are present in the reconstructed volume. Once the clinical operator selects the pixel of interest p on the panoramic radiography 18, a local analysis of the radiography 18 can be performed, aimed at the individuation of fixtures. If some fixture is present, the control unit 8 can automatically increase the X-ray radiation, enlarge the acquisition angle to limit the effect of the metallic objects in reconstruction, or change the weight of the different images in the reconstruction process.

Further modifications relate to operational conditions of the imaging process.

For example, a vertical collimator can be used to irradiate only the upper or lower jaw, thus limiting the dose released into the patient tissue.

Moreover, the user could select onto the panoramic radiography 18 not only a point of interest p, but an entire region of interest 16. The control unit 8 can then generate the acquisition trajectory to reconstruct the entire region of interest 16 selected by the user.

The method used for recording the panoramic radiography 18 can be a standard panoramic, a partial panoramic or an improved orthogonality panoramic, or any other panoramic image provided by the apparatus 1. The panoramic image can finally also be a template panoramic image which is usable for various patients.

It should be noted that the panoramic radiography 18 can be acquired just before the acquisition of the projection images 14 for the tomographic reconstruction method. But the panoramic radiography 18 may also be a panoramic radiography that has been taken by another apparatus or by the same apparatus before an intermediate absence of the patient. The use of another apparatus for the acquisition of the panoramic radiography generally requires that the panoramic radiographic image is associated with information relating to the geometry of the acquisition of the panoramic radiography 18. Such a panoramic radiography 18 can be stored in a storage device, storage medium or some other kind of digital archive and can be retrieved from the digital archive for the selection of the region of interest 16 of the tomographic imaging process. The panoramic radiography 18 may be associated with metadata providing information on the shape of the dentition or spatial arrangement of the teeth allowing the choice of the region of interest based on the panoramic radiography 18. These metadata might be contained in a header of a file containing the panoramic radiography.

The method used for recording tomographic images can be based on various kinds of tomographic examinations such as linear tomography, narrow beam tomography, tomosynthesis, local CB-CT, and other similar methods wherein a trajectory for tomography or tomosynthesis by roto-translation of the imaging system around the head 10 of the patient 2 is executed.

Finally, it should be noted that throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

What is claimed is:

1. A method for dental tomographic X-ray imaging, the method comprising the steps of:
    positioning a patient in an X-ray apparatus by a head support that has been used for the acquisition of a panoramic image and that keeps the patient in the same position as for the acquisition of the panoramic image;
    selecting a region of interest for a local tomographic imaging process based on the panoramic image of the dental arch of the patient at any point of the dental arch;
    calculating the parameters for a trajectory applicable for the local tomographic imaging process by the control unit based on the selection of the region of interest;
    performing an imaging process by the X-ray apparatus under the control of a control unit by moving the imaging system along the trajectory; characterized in that
    the selection of the region of interest includes a selection of the position and orientation of the region of interest in the three-dimensional space, that
    during the acquisition of projection images for the tomographic imaging process the imaging system is moved along a trajectory that involves translations and rotations of the imaging system, and that
    a rotational axis of the imaging system performs an extended movement along a transversal plane wherein the rotational axis is shifted by more than +/−60 millimeter.

2. The method according to claim 1, wherein the panoramic image is associated with information concerning the projection geometry of the panoramic image and is retrieved from a digital archive prior to the selecting step.

3. The method according to claim 1, wherein a template dental arch used for establishing a spatial relation between the image points on the panoramic image and the three-dimensional space.

4. The method according to claim 3, wherein the template dental arch is corrected for the lower or upper jaw taking into account the inclination of the dentition with respect to the vertical direction.

5. The method according to claim 1, wherein a local analysis of the panoramic image is performed by the control unit for identifying fixtures or other metallic objects, and wherein the operational parameters including X-ray dose and angle of view are varied in dependency of the output of the local analysis.

6. The method according to claim 1, wherein, based on the selected region of interest, at least one vertical X-ray collimator is automatically or manually operated avoiding unnecessary exposure of the patient tissues lying outside of the region of interest.

7. The method according to claim 1, wherein the control unit calculates parameters of the trajectory for the tomographic reconstruction of the region of interest selected by the user based on at least one parameter contained in the group comprising the width of the region of interest along the dental arch, the depth of the region of interest in a lateral transverse direction with respect to the dental arch, the volume of the region of interest, the orientation of the region of interest and the projection geometry of the panoramic image.

8. The method according to claim 1, wherein the data of the panoramic radiography are integrated with the data set of radiographic images acquired for the tomography to increase the quality of the reconstructed volume.

9. The method according to claim 1, wherein the reconstructed volume and the panoramic image are displayed together in a three-dimensional representation.

10. The method according to claims 1, wherein the tomographic imaging process is a linear tomography, narrow beam tomography, tomosynthesis or a cone beam computer tomography and the panoramic image is a standard panoramic, a partial panoramic image or a panoramic image with improved orthogonality.

11. The method according to claims 1, wherein a vertically aligned linearly shaped detector is used for the acquisition of the panoramic images and the tomographic imaging process.

12. An apparatus for dental tomographic X-ray imaging comprising:
    an imaging system comprising an X-ray source and an X-ray detector;
    a head support system (9) that positions a head of a patient in a predefined position with respect to the imaging system and that keeps the patient in the same position for the acquisition of a panoramic image and for a local tomographic imaging process; and
    a control unit arranged for selecting a region of interest for the local tomographic imaging process at any point of the dental arch of the patient based on the panoramic image and for controlling the movement of the imaging system during an imaging process characterized in that
    the selection of the region of interest includes a selection of the position and orientation of the region of interest in the three-dimensional space, that
    during the acquisition of projection images for the tomographic imaging process the imaging system is movable along a trajectory that involves translations and rotations of the imaging system, and that a rotational axis of the imaging system is arranged for performing an extended movement along a transversal plane wherein the rotational axis is shifted by more than +/−60 millimeter.

13. The apparatus according to claim 12, wherein the control unit is arranged for performing a local analysis of the panoramic image for identifying fixtures or other metallic objects, and wherein the control unit varies the operational parameters including X-ray dose and angle of view depending on the output of the local analysis.

14. The apparatus according to claim 12 wherein, based on the selected region of interest, at least one vertical X-ray collimator is arranged to be automatically or manually operated avoiding unnecessary exposure of the patient tissues lying outside of the region of interest.

15. The apparatus according to claim 12, wherein the control unit is arranged for calculating the parameters of the trajectory for the reconstruction of the region of interest selected by the user based on at least one parameter contained in the group comprising the width of the region of interest along the dental arch, the depth of the region of interest in a lateral transverse direction with respect to the dental arch, the volume of the region of interest, the orientation of the region of interest and the projection geometry of the panoramic image.

16. The apparatus according to any claim 12, wherein the control unit is arranged for integrating the data of the panoramic radiography with the data set of radiographic images acquired for the tomography to increase the quality of the reconstructed volume.

17. The apparatus according to claim 12, wherein the control unit is arranged for displaying the reconstructed volume and the panoramic image together in a three-dimensional representation.

18. The apparatus according to claim 12, wherein the tomographic imaging process is a linear tomography, narrow beam tomography, tomosynthesis or a cone beam computer tomography and the panoramic image is a standard panoramic, a partial panoramic image or a panoramic image with improved orthogonality.

19. The apparatus according to claim 12, wherein the detector is a vertically aligned linear shaped detector arranged for performing a lateral scanning motion in a horizontal direction during the tomographic imaging process.

20. The apparatus according to claim 12, wherein the head support system includes a bite unit, a head rest and a laser light source for marking a reference point on the head of the patient.

* * * * *